United States Patent [19]
Root

[11] Patent Number: 5,674,178
[45] Date of Patent: Oct. 7, 1997

[54] ARTIFICIAL INSEMINATION TOOL

[76] Inventor: Robert W. Root, 6060 N. Drury, Kansas City, Mo. 64119

[21] Appl. No.: 662,032

[22] Filed: Jun. 12, 1996

[51] Int. Cl.$^6$ ............................................. A61B 17/43
[52] U.S. Cl. ............................................................ 600/35
[58] Field of Search .................... 600/35, 114, 125–129, 600/139–141

[56] References Cited

U.S. PATENT DOCUMENTS

| | | | |
|---|---|---|---|
| 3,892,238 | 7/1975 | Banford | 600/35 |
| 4,682,585 | 7/1987 | Hiltebrandt | 600/114 |

FOREIGN PATENT DOCUMENTS

| | | | |
|---|---|---|---|
| 2667782A | 4/1992 | France | 600/25 |
| 2701385A3 | 8/1994 | France | 600/35 |

OTHER PUBLICATIONS

Pp. 96 and front and back pages of Nasco Farm & Ranch 1995 catalog; exact date of publication unknown, but at least one year prior to the filing of the present application.

*Primary Examiner*—Lee S. Cohen
*Assistant Examiner*—David M. Ruddy
*Attorney, Agent, or Firm*—Litman, McMahon and Brown, L.L.C.

[57] ABSTRACT

An improved artificial insemination tool includes a tip made of a medical grade thermoplastic elastomer (TPE) which is insert molded around one end of a elongate tube made of High Density Polyethylene (HDPE). The TPE material is extremely durable and includes a series of annular rings which are progressively graduated in size from a small diameter to a larger diameter. The annular rings are separated by respective annular recesses. The graduated size of the tip allows it to be used with both young and mature animals.

6 Claims, 1 Drawing Sheet

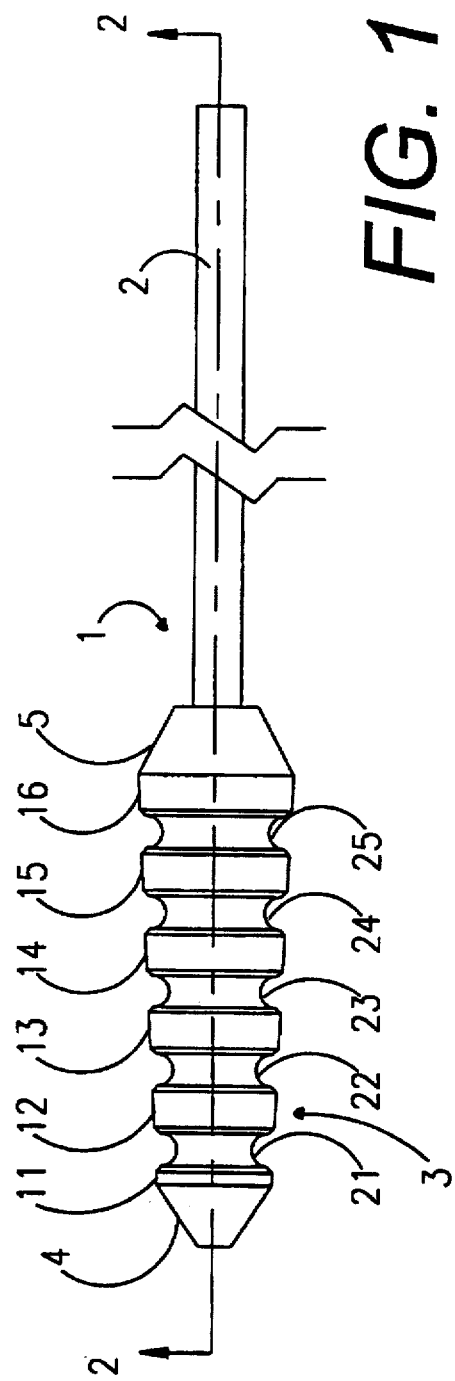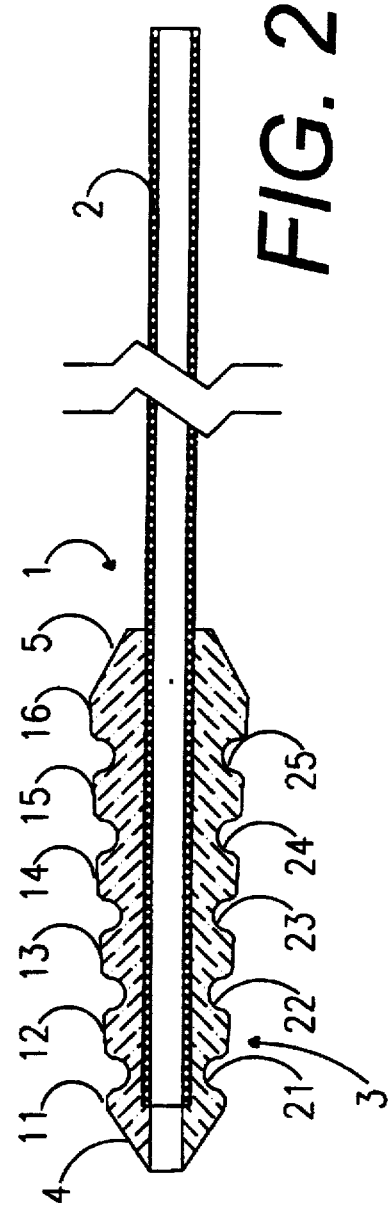

ARTIFICIAL INSEMINATION TOOL

BACKGROUND OF THE INVENTION

1. Field of the Invention

The present invention relates to an improved artificial insemination tool, specifically designed for use with swine. More particularly, the improved device includes a elongate tube made of medical grade thermoplastic elastomer which is insert molded around a High Density Polyethylene (HDPE) tube and shaped as a series of annular rings of graduated diameter.

2. Description of the Related Art

The use of artificial insemination as a breeding management technique in the swine industry is on the increase. As production facilities increase in size and scale, efforts to maximize production and minimize costs in swine herds have received increased scrutiny.

Artificial insemination (AI) achieves a number of advantages in this regard. For example, a single boar, by using natural service techniques, can inseminate up to 500 sows per year. The same boar, by using AI techniques, can service up to 3000 sows in a year, with about the same farrowing rate. Thus, a breeder can concentrate his resources in fewer, and presumably higher quality, boars by using AI techniques. Also, semen can be secured from boars outside of the herd to economically increase the quality and diversity of breeding stock. Furthermore, reducing the number of boars needed decreases the barn space requirement for boars, consequently increasing the barn space available for farrowing sows. For example, typical recommended floor space for a confined boar is about 50 square feet while a farrowing sow needs only about 18 square feet. Thus every boar eliminated frees up space for about three farrowing sows, each of which can produce between 2 and 3 litters per year. Other advantages include greater flexibility in breeding scheduling and no limitations on the use of older, heavier boars with younger, lighter sows.

Numerous tools for the artificial insemination of swine have been developed. Early versions included a simple pipe or tube, open at both ends, which was inserted into the uterus with boar semen then introduced into the outer end of the tube. Problems with this arrangement include causing tissue injury from contact with the exposed insertion end of the tube and the possibility of inadvertently inserting a bare flexible tube into the bladder tract. In addition, these tubes are typically considerably smaller in diameter than the cervix, thus allowing undesirable backflow of injected semen out of the cervix.

In order to address these problems, it is known to add a molded polyurethane foam tip which is attached to and surrounds the inner end of the tube. Such a molded foam tip reduces tissue damage and prevents inadvertent insertion of the tube into the bladder tract. Since the molded foam tip also more closely approximates the cervix diameter, semen backflow is reduced.

A potentially serious problem with such polyurethane foam tips is their tendency to tear, leaving the end of the foam tip in the sow's reproductive tract. When this happens, the sow will typically discharge and abort, causing the temporary, or permanent removal of the sow from the breeding pool.

Another problem with known AI foam tips is the requirement for different diameter tips to service different sows. Typically, smaller tips must be used to service Gilts (young first parody sows) while larger diameter tips are needed for mature sows. This requires a breeder to stock different sizes of AI tools.

It is clear then, that a need exists for an AI tool for sows which alleviates the above problems. Such an AI tool should be designed to prevent tissue damage during insertion, yet must not tear or disintegrate within the sow's reproductive tract. Furthermore, the AI tool should preferably be a "one size fits all" tool useful for inseminating both gilts and mature sows.

SUMMARY OF THE INVENTION

The present invention is an improved artificial insemination tool designed for use with swine and other animals. The AI tool includes a tip made of a medical grade thermoplastic elastomer (TPE) which is insert molded around one end of a tube made of High Density Polyethylene (HDPE). By insertion molding the TPE about the HDPE tube, the tip is securely fastened to the tube. The TPE material is extremely durable and is not subject to breaking or tearing as are prior art polyurethane molded tips. The tip is preferably 2 to 4 inches long and is molded as a series of annular rings progressively graduated in size from smaller to larger diameters. Each successive annular ring is separated from the next ring by an annular recess such that an effective seal is formed with the sow's cervix upon insertion to prevent backflow of semen around the tip. The graduated size of the tip allows it to be used with gilts and mature sows since it adapts to the size of the cervix depending upon the distance the tip is inserted into the uterus.

OBJECTS AND ADVANTAGES OF THE INVENTION

The principal objects of the present invention are: to provide an improved artificial insemination tool for swine and other animals; to provide such an AI tool with an extremely durable, yet flexible tip which prevents tissue injury to the sow; to provide such an AI tool in which the tip is made of a medical grade thermoplastic elastomer (TPE); to provide such an AI tool in which the TPE tip is insert molded around a tube made of high density polyethylene (HDPE); to provide such an AI tool with a TPE tip which is molded as a series of annular rings which are graduated in size from the insertion end backward to allow its universal use with gilts up to mature sows; to provide such an AI tool which effectively seals off the sow's cervix to prevent backflow of semen from the uterus; and to provide such an improved AI tool which is particularly well adapted for its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of an artificial insemination tool in accordance with the present invention.

FIG. 2 is a cross sectional view of the artificial insemination tool, taken along line 2—2 of FIG. 1.

DETAILED DESCRIPTION OF THE INVENTION

As required, detailed embodiments of the present invention are disclosed herein; however, it is to be understood that the disclosed embodiments are merely exemplary of the invention. which may be embodied in various forms. Therefore, specific structural and functional details disclosed herein are not to be interpreted as limiting. but merely as a basis for the claims and as a representative basis for teaching one skilled in the art to variously employ the present invention in virtually any appropriately detailed structure.

I. Improved Artificial Insertion Tool

Referring to FIG. 1, there is shown an improved artificial insemination tool in accordance with the present invention, generally indicated at 1. The tool 1 includes an elongate tube 2 which is preferably made of high density polyethylene (HDPE). The tube 2 is typically approximately 2 feet in length with an outside diameter of approximately ¼" and an inside diameter of approximately ⅛".

The HDPE tube 2 is insert molded within a resilient tip 3 made of medical grade thermoplastic elastomer (TPE). The TPE tip 3 is typically 2" to 4" in length and is preferably about 3" in length.

The TPE tip 3 includes a hollow tapered insertion end 4 and is graduated in size from the tapered insertion end 4 to a tapered rear end 5. Between the insertion end 4 and the rear end 5 of the tip 3 are a series of annular rings 11–16, which gradually increase in diameter. Between the rings 11–16 are intervening annular recesses 21–25.

II. Use of AI Tool

In order to use the AI tool 1 to artificially inseminate a gilt or a sow, the tip 3 is inserted into the uterus of the gilt or sow via the cervix. The diameter of the cervix depends upon the size, maturity and farrowing history of the gilt or sow. The tip 3 is inserted until significant resistance is encountered, which insures that the annular ring 11–16 which is appropriately sized to seal off the cervix of that particular sow is, in fact, in contact with the cervix. This insures that the cervix is sealed by the tip 3 to prevent backflow of semen from the uterus. The resilient nature of the TPE tip 3 also insures that no tissue damage is incurred during insertion of the tool 1. Once the tip 3 is securely in place within the sow's cervix, semen is introduced into a distal end 31 of the tube 2 from one of a variety of well known semen injection tools, with the injected semen then flowing down the tube 2, through the tip 3 and into the uterus of the sow being serviced.

By insert molding the TPE material about the periphery of the tube 2, the innermost portion of the tip 3 becomes a highly effective bonding agent, securely bonding the molded TPE tip 3 to the HDPE tube 2. Meanwhile, the TPE material of the tip 3 is extremely durable and cohesive, thus insuring that the tip 3 will not break up or tear within the reproductive tract of the sow.

It should be noted that the dimensions mentioned for the tube 2 and the tip 3 are merely representative and are not intended to be limiting. It should also be noted that, although the inventive AI tool 1 has been described as being useful for insemination of swine, it could also be used for other animals, such as cattle or sheep, for example.

It is thus to be understood that while certain forms of the present invention have been illustrated and described herein, it is not to be limited to the specific forms or arrangement of parts described and shown.

What is claimed and desired to be secured by Letters Patent is as follows:

1. An improved artificial insemination tool comprising:
   (a) an elongate hollow tube open at both ends; and
   (b) a resilient tip molded around an insert end of said elongate tube , said resilient tip including:
      i) a plurality of separate annular rings formed therein with said annular rings graduating in size from a minimum to a maximum size from an insertion end to a rear end of said tip; and
      ii) a plurality of separate annular recesses with each said recess being positioned between a respective pair of said annular rings such that each of said rings is separated from the adjacent ring or rings by one of said annular recesses.

2. An improved artificial insemination tool as in claim 1, wherein said elongate tube is formed of high density polyethylene (HDPE).

3. An improved artificial insemination tool as in claim 1, wherein said insertion end and said rear end of said resilient tip are conically shaped.

4. An improved artificial insemination tool comprising:
   (a) an elongate hollow tube open at both ends, said elongate tube comprising high density polyethylene (HDPE); and
   (b) a resilient tip insert molded around an insert end of said elongate tube, said resilient tip comprising:
      i) a plurality of separate annular rings formed therein with said annular rings graduating in size from a minimum to a maximum size from an insertion end to a rear end of said tip; and
      ii) a plurality of separate annular recesses with each said recess being positioned between a respective pair of said annular rings such that each of said rings is separated from the adjacent ring or rings by one of said annular recesses.

5. An improved artificial insemination tool as in claim 4, wherein said insertion end and said rear end of said resilient tip are conically shaped.

6. An improved artificial insemination tool comprising:
   (a) an elongate hollow tube open at both ends, said elongate tube comprising high density polyethylene (HDPE); and
   (b) a resilient tip insert molded around an insert end of said elongate tube, said resilient tip comprising a thermoplastic elastomer (TPE) and wherein said resilient tip includes a plurality of separate annular rings formed therein with said annular rings graduating in size from a minimum to a maximum size from an insertion end to a rear end of said tip, and a plurality of separate annular recesses with each said recess being positioned between a respective pair of said annular rings such that each of said rings is separated from the adjacent ring or rings by one of said annular recesses; and
   (c) wherein said insertion end and said rear end of said resilient tip are conically shaped.

\* \* \* \* \*